United States Patent
Wu et al.

(10) Patent No.: US 9,012,516 B2
(45) Date of Patent: Apr. 21, 2015

(54) COPOLYMER, COMPOSITION AND METHOD FOR MODIFYING RHEOLOGY

(75) Inventors: Decheng Wu, Singapore (SG); Ye Liu, Singapore (SG); Jianwei Xu, Singapore (SG); Chaobin He, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 100 days.

(21) Appl. No.: 13/997,179

(22) PCT Filed: Dec. 21, 2011

(86) PCT No.: PCT/SG2011/000445
§ 371 (c)(1),
(2), (4) Date: Jun. 21, 2013

(87) PCT Pub. No.: WO2012/087244
PCT Pub. Date: Jun. 28, 2012

(65) Prior Publication Data
US 2013/0296444 A1  Nov. 7, 2013

Related U.S. Application Data

(60) Provisional application No. 61/425,497, filed on Dec. 21, 2010.

(51) Int. Cl.
*A61K 8/81* (2006.01)
*A61K 47/32* (2006.01)
*C08F 290/14* (2006.01)

(52) U.S. Cl.
CPC ........... *A61K 8/8152* (2013.01); *C08F 290/148* (2013.01); *A61K 47/32* (2013.01)

(58) Field of Classification Search
CPC ..... A61K 8/8152; A61K 47/32; C08F 290/148
See application file for complete search history.

(56) References Cited

U.S. PATENT DOCUMENTS

| | | | |
|---|---|---|---|
| 3,808,178 A | 4/1974 | Gaylord | |
| 4,153,641 A | 5/1979 | Deichert et al. | |

(Continued)

FOREIGN PATENT DOCUMENTS

| EP | 1 914 264 A1 | 4/2008 |
|---|---|---|
| EP | 2 103 636 A1 | 9/2009 |
| WO | WO 02/50144 A2 | 6/2002 |

OTHER PUBLICATIONS

PCT International Search Report for PCT Counterpart Application No. PCT/SG2011/000445, 3 pgs., (Jan. 30, 2012).

(Continued)

*Primary Examiner* — Robert S Loewe
(74) *Attorney, Agent, or Firm* — Blakely, Sokoloff, Taylor & Zafman LLP

(57) ABSTRACT

A copolymer for modifying rheology is formed of monomer units consisting essentially of at least one first monomer unit comprising a polyhedral oligomeric silsesquioxane having an ethylenically unsaturated radical; at least one second monomer unit comprising an unsaturated oligo-poly(dimethyl siloxane)(meth)acrylate; and a sufficient amount of at least one unsaturated water-soluble monomer, such that the copolymer is soluble in water. A composition may comprise an electrolyte and the copolymer. The rheology of an environment comprising an electrolyte may be modified by adding the copolymer to the environment.

18 Claims, 7 Drawing Sheets

(I)

(II)

(56) References Cited

U.S. PATENT DOCUMENTS

| | | | |
|---|---|---|---|
| 4,254,248 | A | 3/1981 | Friends et al. |
| 4,277,595 | A | 7/1981 | Deichert et al. |
| 5,412,053 | A | 5/1995 | Lichtenhan et al. |
| 5,484,867 | A | 1/1996 | Lichtenhan et al. |
| 5,589,562 | A | 12/1996 | Lichtenhan et al. |
| 6,545,114 | B1 | 4/2003 | Yang et al. |
| 6,586,548 | B2 | 7/2003 | Bonafini, Jr. et al. |
| 6,916,543 | B2* | 7/2005 | De et al. .......... 428/447 |
| 7,381,471 | B2* | 6/2008 | Augustine et al. .......... 428/447 |
| 7,604,917 | B2* | 10/2009 | Choi et al. .......... 430/270.1 |
| 7,868,112 | B2* | 1/2011 | Oikawa et al. .......... 526/279 |
| 2002/0128414 | A1* | 9/2002 | James et al. .......... 526/279 |
| 2002/0182541 | A1* | 12/2002 | Gonsalves .......... 430/287.1 |
| 2006/0088787 | A1* | 4/2006 | Gonsalves et al. .......... 430/281.1 |
| 2006/0166128 | A1* | 7/2006 | Gogolides et al. .......... 430/270.1 |
| 2009/0191474 | A1* | 7/2009 | Sun et al. .......... 430/5 |
| 2010/0166685 | A1 | 7/2010 | Farcet |

OTHER PUBLICATIONS

PCT Written Opinion of the International Searching Authority for PCT Counterpart Application No. PCT/SG2011/000445, 4 pgs., (Jan. 30, 2012).

PCT Notification concerning Transmittal of International Preliminary Report on Patentability (Chapter I of the Patent Cooperation Treaty) for PCT Counterpart Application No. PCT/SG2011/000445, 6 pgs., (Jul. 4, 2013).

Yoshitaka Gushikem, et al., "Synthesis and Applications of Functionalized Silsesquioxane Polymers Attached to Organic and Inorganic Matrices", Pure and Applied Chemistry, vol. 80, No. 7, pp. 1593-1611, (2008).

* cited by examiner (I)

(II)

(III)

(IV)

(V)

(VI)

COPOLYMER, COMPOSITION AND METHOD FOR MODIFYING RHEOLOGY

CROSS-REFERENCE TO RELATED APPLICATIONS

This patent application is a U.S. National Phase Application under 35 U.S.C. §371 of International Application No. PCT/SG2011/000445, filed Dec. 21, 2011, entitled COPOLYMER, COMPOSITION AND METHOD FOR MODIFYING RHEOLOGY, which claims the benefit of, and priority from, United States Provisional Patent application Ser. No. 61/425,497, filed Dec. 21, 2010, and entitled "Copolymers as Rheology Modifiers," the entire contents of which were incorporated by reference.

FIELD OF THE INVENTION

The present invention relates generally to rheology modifiers, and particularly to rheology modifying copolymers and related compositions and methods.

BACKGROUND OF THE INVENTION

A rheology modifier (RM) can be used to increase the viscosity of a composition containing the RM. Conventional rheology modifying compositions that allow modification of viscosity of electrolyte-containing environments include cross-linked linear poly(vinyl amide/unsaturated carboxylic acid) copolymers, and cross-linked copolymers formed of unsaturated carboxylic acid, a hydrophobic mercaptan monomer, a thioester or amino acid containing chain transfer agent into the copolymer composition, and a cross-linking agent. For example, hydrophobically modified hydroxyethyl cellulose or ethylhydroxyethyl cellulose, hydrophobically modified ethoxylate urethanes, and hydrophobically modified alkali-soluble or swellable emulsions are known to modify rheology.

SUMMARY OF THE INVENTION

According to one aspect of the invention, there is provided a copolymer for modifying rheology, formed of monomer units consisting essentially of at least one first monomer unit comprising a polyhedral oligomeric silsesquioxane having an ethylenically unsaturated radical; at least one second monomer unit comprising an unsaturated oligo-poly(dimethyl siloxane)(meth)acrylate; and a sufficient amount of at least one unsaturated water-soluble monomer, such that the copolymer is soluble in water.

In some embodiments, the copolymer may comprise about 1 to about 30 wt % of the at least one first monomer unit, about 1 to about 40 wt % of the at least one second monomer unit, and about 30 to about 98 wt % of the at least one unsaturated water-soluble monomer, based on the total weight of the monomer units and the at least one unsaturated water-soluble monomer.

In some embodiments, the copolymer may comprise about 5 to about 8 wt % of the at least one first monomer unit, about 4 to about 35 wt % of the at least one second monomer unit, and about 60 to about 90 wt % of the at least one unsaturated water-soluble monomer, based on the total weight of the monomer units and the at least one unsaturated water-soluble monomer.

The at least one first monomer unit may comprise a monomer unit of formula (I):

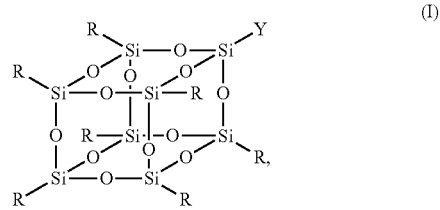

wherein Y is independently an ethylenically unsaturated radical, for example, acryloxypropyl; and each R is independently a $C_1$-$C_{12}$ monovalent hydrocarbon radical such as i-butyl, a $C_1$-$C_{12}$ monovalent hydrocarbon radical comprising an ether linkage, a halogen-substituted $C_1$-$C_{12}$ monovalent hydrocarbon radical, or a halogen-substituted $C_1$-$C_{12}$ monovalent hydrocarbon radical comprising an ether linkage.

The at least one first monomer unit may also comprise a monomer unit of formula (II), (III) or (IV):

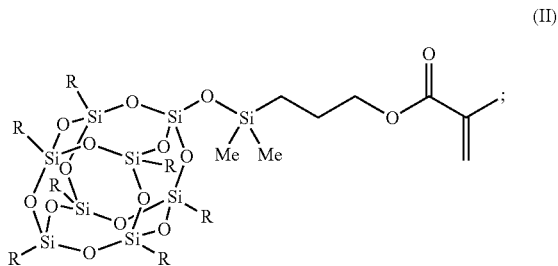

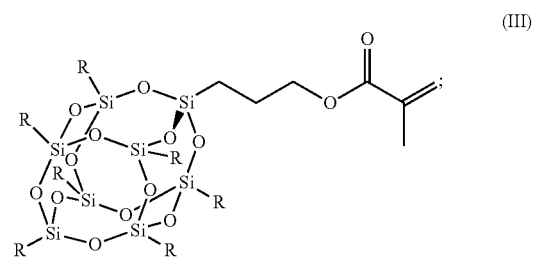

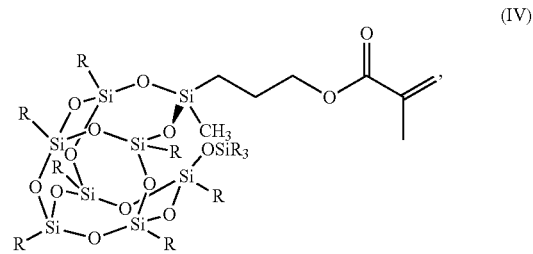

wherein each R is independently a $C_1$-$C_{12}$ monovalent hydrocarbon radical, a $C_1$-$C_{12}$ monovalent hydrocarbon radical comprising an ether linkage, a halogen-substituted $C_1$-$C_{12}$ monovalent hydrocarbon radical, or a halogen-substituted $C_1$-$C_{12}$ monovalent hydrocarbon radical comprising an ether linkage. In some embodiments, the R may each be i-butyl in formula (II), (III) or (IV).

The copolymer may comprise 5 repeating units of the at least one first monomer unit.

The at least one second monomer unit may comprise a monomer unit of formula (V):

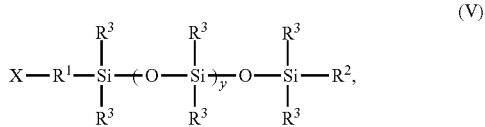

wherein X is an activated unsaturated radical, for example, (meth)acryloxy; $R^1$ is a $C_1$-$C_{22}$ divalent hydrocarbon radical, for example, propylene; $R^2$ is a $C_1$-$C_{22}$ monovalent hydrocarbon radical, for example, n-butyl; each $R^3$ is methyl; and y is from 1 to 200.

The copolymer may comprise 1 to 5 repeating units of the at least second monomer unit.

The at least one unsaturated water-soluble monomer comprises a monomer having the formula (VI):

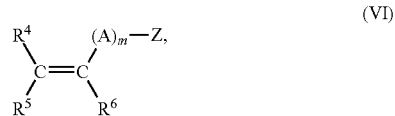

wherein m is an integer from 0 to 10; A is a methylene group; $R^4$ is a hydrogen atom, a phenyl group, or a benzyl group; $R^5$ is a hydrogen atom, or a lower alkyl or carboxyl group; $R^6$ is a hydrogen atom, a lower alkyl group, —$CH_2COOH$, a phenyl group, a benzyl group, or a polymeric group comprising a unit derived from a sulfonic acid; and Z is COOH, $COO(B)_nY^1$, or $CON(R^7)R^8$, wherein $R^7$ and $R^8$ is each independently hydrogen or $(B)_nY^1$; B is a methylene group; n is an integer from 1 to 10; and $Y^1$ is a hydroxyl group, primary amine, tertiary amine, or quaternary ammonium salt.

The at least one unsaturated water-soluble monomer may comprise a carboxylic acid such as an acrylic acid.

The copolymer may be a random copolymer, a block copolymer or a graft copolymer.

According to another aspect of the invention, there is provided a composition comprising an electrolyte and the copolymer described herein.

According to another aspect of the invention, there is provided a method of modifying the rheology of an environment comprising an electrolyte, the method comprising adding the copolymer to the environment. The environment may comprise a solution and the copolymer is added to the solution.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

In overview, it has been recognized that a rheology modifier can be formed from a copolymer consisting essentially of (a) a monomer unit comprising a polyhedral oligomeric silsesquioxane (POSS) having an ethylenically unsaturated radical; (b) a monomer unit comprising an unsaturated oligo-poly (dimethyl siloxane)(meth)acrylate (PDMS-MA); and (c) a sufficient amount of an unsaturated water-soluble monomer, where the copolymer is soluble in water. In a specific embodiment, the water-soluble monomer may be an acrylic acid.

The numbers of (a) and (b) monomer units in the copolymer may vary. In some cases, the copolymer may include about 1 to about 99 wt % of the unsaturated water-soluble monomer, about 1 to about 99 wt % of the POSS-bearing monomer, about 1 to about 99% of the PDMS-MA monomer, based on the total weight of these monomers.

In a selected embodiment, the copolymer may contain about 30 to about 98 wt % of the unsaturated water-soluble monomer, about 1 to about 30 wt % of the POSS-bearing monomer, and about 1 to about 40 wt % of the PDMS-MA monomer. For example, the copolymer may contain about 5 to about 8 wt % of POSS monomer units, about 4 to about 35 wt % of PDMS-MA monomer units, and about 60 to about 90 wt % of unsaturated water-soluble monomers, based on the total weight of the monomer units and the unsaturated water-soluble monomer.

Conveniently, such a copolymer may be combined with an electrolyte in a composition to form a rheology modifying composition, or added to an environment containing an electrolyte, to modify the rheology of the environment. The environment may be a solution such as an aqueous solution, or an ionic liquid. The copolymer may be added to increase the viscosity of the solution.

The copolymer may be a random copolymer, a block copolymer or a graft copolymer. The copolymer may be amphiphilic.

An embodiment is thus related to a composition containing the copolymer and an electrolyte.

Another embodiment relates to a method of modifying an environment containing an electrolyte. In this method, the copolymer is added to the environment as a rheology modifier. The environment may be a solution and the copolymer may be added to the solution.

The present inventors have found that a copolymer consisting essentially of components (a), (b) and (c) as described herein can be effective for use as a rheology modifier in an aqueous environment without any additional copolymer component.

Component (a)—POSS monomer(s)

A polyhedral oligomeric silsesquioxane (POSS) has a three-dimensional molecular structure in which at least two siloxane rings are connected to form a relatively rigid structure (referred to as a cage structure herein). Suitable POSS-bearing monomers include those that contain at least one substituent group comprising a polymerizable activated unsaturated group.

Example structures of suitable POSS monomers are illustrated in FIGS. 1A, 1B, 1C and 1D.

Figure 1A:
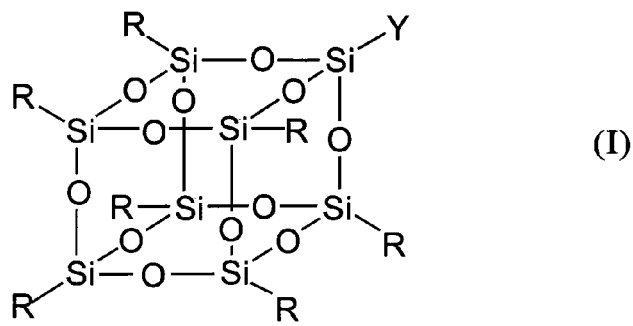
FIGS. 1A, 1B, 1C and 1D are schematic diagrams showing possible chemical structures of a first component of a rheology modifying copolymer, according to embodiments of the present invention.

In selected embodiments, the general structure of a suitable silsesquioxane-based monomeric unit may have the cage structure indicated as Formula (I) in FIG. 1A. In Formula (I), Y is an ethylenically unsaturated radical. Each R may be independently a $C_1$-$C_{12}$ monovalent hydrocarbon radical, which may contain ether linkages, may be halogen-substituted, or may be halogen-substituted and contain ether linkages.

A suitable POSS monomer should contain at least one polymerizable site. An ethylenically unsaturated group conveniently provides a polymerizable site. An ethylenically unsaturated radical is an unsaturated group that includes a substituent for facilitating free radical polymerization, such as a vinyl-containing substituent.

Example suitable Y radicals include (meth)acryloxy, (meth)acrylamido and styryl. As used herein, the term "(meth)" denotes optional methyl substituent. The (meth)acryloxy, (meth)acrylamido and styryl radicals may be substituted with an alkyl group. A (meth)acryloxy radical, for example, acryloxypropyl, may be advantageous over other radicals in some embodiments.

Example R radicals include alkyl, cycloalkyl, aryl, aralkyl, alkary, alkoxyalkyl radicals, and their halogen-substituted derivatives. In some embodiments, a $C_1$-$C_4$ alkyl, such as isobutyl, may be used.

The POSS monomer in Formula (I) may have a closed-cage structure, or an open-cage structure.

Suitable POSS monomers may have different cage sizes, either larger or smaller than the size of the structure in Formula (I).

Figure 1B:
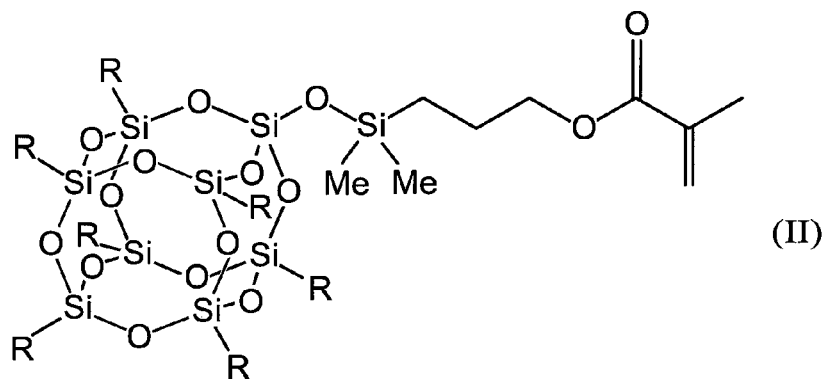
Figure 1C:
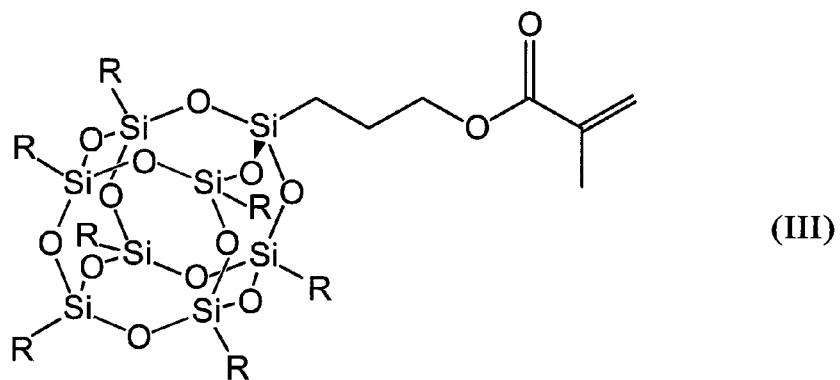
Figure 1D:
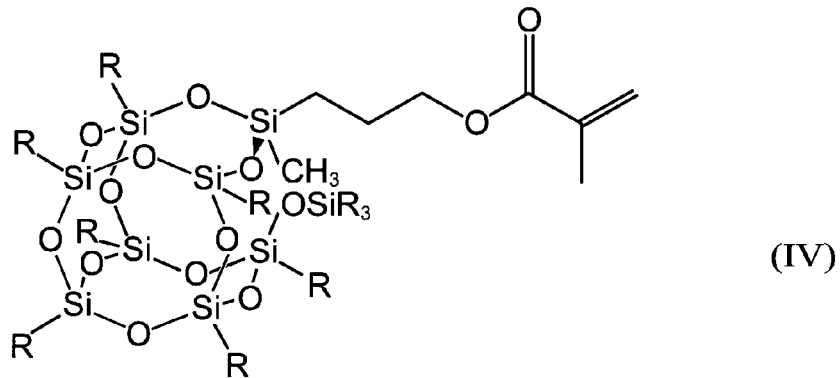

Suitable POSS monomers may also have structures as illustrated by Formulae (II), (III), and (IV) in FIGS. 1B, 1C and 1D. Each R in these structures may be independently a $C_1$-$C_{12}$ monovalent hydrocarbon radical, which may contain ether linkages, may be halogen-substituted, or may be halogen-substituted and contain ether linkages. For example, each R may be i-butyl.

As can be understood, the structures of Formulae (II) and (III) are examples of closed-cage structures. In a "closed-cage", each ring silicon atom is linked to three other adjacent ring silicon atoms through respective oxygen atoms.

In some embodiments, the POSS monomer may have the structure of Formula (III).

The structures of Formula (IV) are examples of open-cage structures. In an "open-cage" structure, two or more ring silicon atoms are each linked to less than three other ring silicon atoms through oxygen atoms. In other words, each of these two or more ring silicon atoms is linked to a group that is not an oxygen bonded to an adjacent ring silicon atom.

The POSS monomers can be produced by a suitable technique known to those skilled in the art. Example techniques are described in U.S. Pat. Nos. 5,412,053, 5,484,867, 5,589,562, and 6,586,548.

Figure 2:
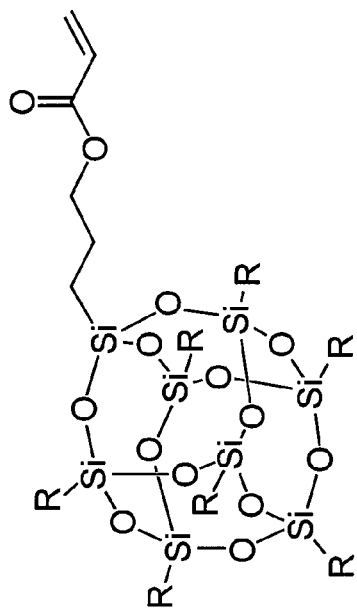
FIG. 2 is a schematic diagram illustrating a synthesis route for forming a polyhedral oligomeric silsesquioxane (POSS) monomer.
Figure 2:
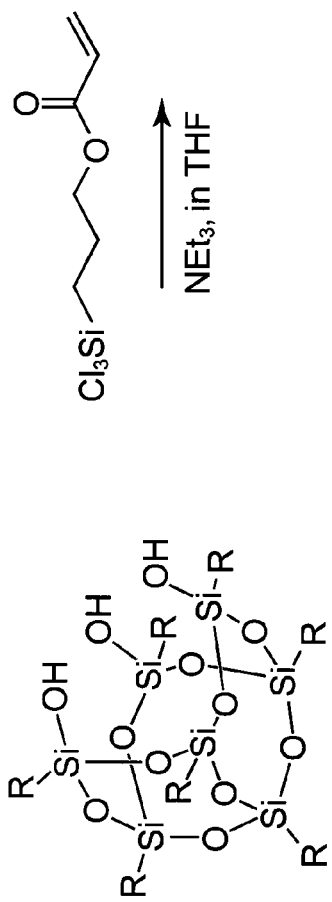

In a selected embodiment, the POSS monomer may be formed according to the synthesis route illustrated in FIG. 2, and have the chemical structure shown on the right hand side of FIG. 2. The R radical can be i-butyl. The yield of this process can be greater than 90%.

Component (b)—PDMS-MA monomer(s)

As used herein, a PDMS-MA monomer denotes a mono(meth)acryloxyalkyl-terminated poly(dimethylsiloxane). A mono(meth)acryloxypropyl-terminated poly(dimethylsiloxane) may be advantageously used in some embodiments.

Figure 3:
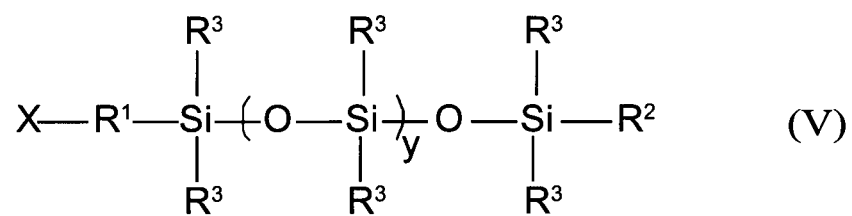
FIG. 3 is a schematic diagram showing the chemical structure of a second component of the copolymer.

The PDMS-MA monomer may have the Formula (V) shown in FIG. 3.

In Formula (V), X may be an activated unsaturated radical. $R^1$ may be a $C_1$-$C_{22}$ divalent hydrocarbon radical. $R^2$ may be a $C_1$-$C_{22}$ monovalent hydrocarbon radical. Each side group $R^3$ may be a methyl radical. The number y in Formula (V) may be an average number in the range from 1 to 200.

For clarity, it should be understood that in chemical formulae or expressions, the superscripts in expressions such as "$R^1$" to "$R^{11}$" are position indices, and the subscripts in expressions such as "$C_1$" to "$C_{12}$" indicate the numbers of repeated atoms, units, or groups.

Suitable PDMS-MA monomer units may include polysiloxanes end-capped/terminated with polymerizable unsaturated groups, and may be poly(organosiloxane) and polyparaffinsiloxane monomers.

Suitable oligo-siloxane monomers can be produced by a suitable technique known to those skilled in the art. For example, some oligo-siloxane monomers can be produced according to the techniques disclosed in U.S. Pat. No. 3,808,178, 4,153,641, 4,254,248, 4,277,595, and 6,545,114.

Suitable PDMS-MA monomers are also available from commercial sources such as SIGMA-ALDRICH™.

An activated unsaturated radical is an unsaturated group that includes a substituent for facilitating free radical polymerization, such as a vinyl-containing substituent. Suitable X radicals include (meth)acryloxy, (meth)acrylamido, and styryl. A (meth)acryloxy radical may be advantageously used as X in some embodiments.

Suitable $R^1$ radicals include alkylene radicals. For example, suitable $R^1$ radicals may include methylene, propylene, and butylene. In some embodiments, $R^1$ can be propylene.

Suitable $R^2$ radicals include alkyl radicals. For example, suitable $R^2$ radicals may include methyl, propyl, and butyl. In some embodiments, $R^2$ can be n-butyl.

Each $R^3$ radical may be methyl.

Component (c)—Unsaturated water-soluble monomers

A "water-soluble" monomer refers to a monomer that has a water solubility of about one wt % or greater. That is, at least about 1 g of the monomer can dissolve in 100 g of water. In another embodiment of the present invention, the water solubility of the monomer is at least about 10 g in 100 g of water, and in yet another embodiment, the water solubility is at least about 50 g in 100 g of water.

Figure 4:
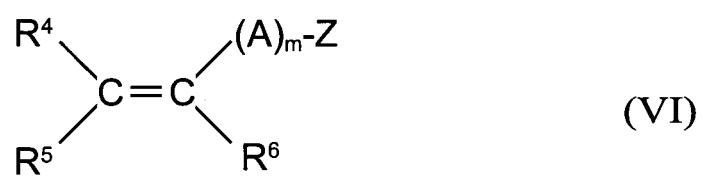
FIG. 4 is a schematic diagram showing the chemical structure of a third component of the copolymer.

In one embodiment, the unsaturated water-soluble monomer may be a carboxylic acid, such as an acrylic acid. In other embodiments, the unsaturated water-soluble monomer may have the general structure represented by Formula (VI) in FIG. 4. In Formula (VI), m is an integer from 0 to 10. "A" is a methylene group, which may be optionally bonded to a carbon atom of an unsaturated group, or to a neighboring methylene group when m is greater than 1. The bonding may be through a non-carbon atom such as oxygen or sulfur. $R^4$ may be a hydrogen atom, a phenyl group, or a benzyl group. $R^5$ may be a hydrogen atom, or a lower alkyl or carboxyl group. $R^6$ may be a hydrogen atom, a lower alkyl group, —$CH_2COOH$, a phenyl group, or a benzyl group. $R^6$ may also be a polymer containing units derived from a sulfonic acid, such as vinylsulfonic, styrenesulfonic, or acrylamidoalkylsulfonic units.

In Formula (VI), Z may be COOH, $COO(B)_nY^1$, or $CON(R^7)R^8$. $R^7$ and $R^8$ are each independently hydrogen or $(B)_nY^1$. B is a methylene group, and may be optionally bonded to a carbon atom of an unsaturated group or to a neighboring methylene group when n is greater than 1, through a non-carbon atom such as oxygen or sulfur. The number n is an integer from 1 to 10. $Y^1$ is a hydroxyl (OH) group, primary amine ($NH_2$), secondary amine ($NHR^9$), tertiary amine ($R^9NR^{10}$), or quaternary ammonium salt ($R^9N^+(R^{10})R^{11}D^-$). $R^9$, $R^{10}$ and $R^{11}$, which may be identical or different, are each independently a linear or branched alkyl group having from 1 to 22 carbon atoms, such as 4 to 20 or 6 to 18 carbon atoms. The linear or branched alkyl group may be optionally interrupted by at least one non-carbon atom such as O, N, S or P. The alkyl group may be optionally substituted by at least one substituent, which may be a hydroxyl group or a halogen atom (Cl, Br, I or F).

$D^-$ is an anion, which may be a halide ion and D may be a halogen, such as Cl, Br, F, or I. $D^-$ may also be a sulfate, sulfonate, phosphonate, hydroxide, borate, cyanide, carbonate, thiocyanate, thiosulfate, isocyanate, sulfite, bisulfate, nitrate, oxalate, silicate, sulfide, cyanate, acetate, or another inorganic or organic anion.

The unsaturated water-soluble monomer may be an acid monomer, such as (meth)acrylic, crotonic, itaconic, maleic, and fumaric acid monomer or the like.

The unsaturated water-soluble monomer may also be an amino-substituted (meth)acrylamide, such as dimethylaminopropyl(meth)acrylamide, dimethylaminoethyl(meth)acrylamide, N,N-bis(dimethylaminoethyl)(meth)acrylamide, or N,N-bis(dimethyl-aminopropyl)(meth)acrylamide.

The unsaturated water-soluble monomer may also be an amino-substituted (meth)acrylate, such as dimethylaminoethyl(meth)acrylate or dimethylaminopropyl(meth)acrylate.

The unsaturated water-soluble monomer may also be a hydroxyalkyl(meth)acrylate, such as hydroxyethyl(meth)acrylate or hydroxypropyl(meth)acrylate.

Mixtures of different unsaturated water-soluble monomers may be included in the copolymer or the mixture for forming the copolymer.

Suitable unsaturated water-soluble monomers such as acrylic acids are available from commercial sources such as SIGMA-ALDRICH™.

Some Possible Configurations and Synthesis Methods of Rheology Modifying Copolymers A rheology modifying copolymer as described above may have a molecular weight in the range of about 100 to about 5,000 K.

Figure 5:
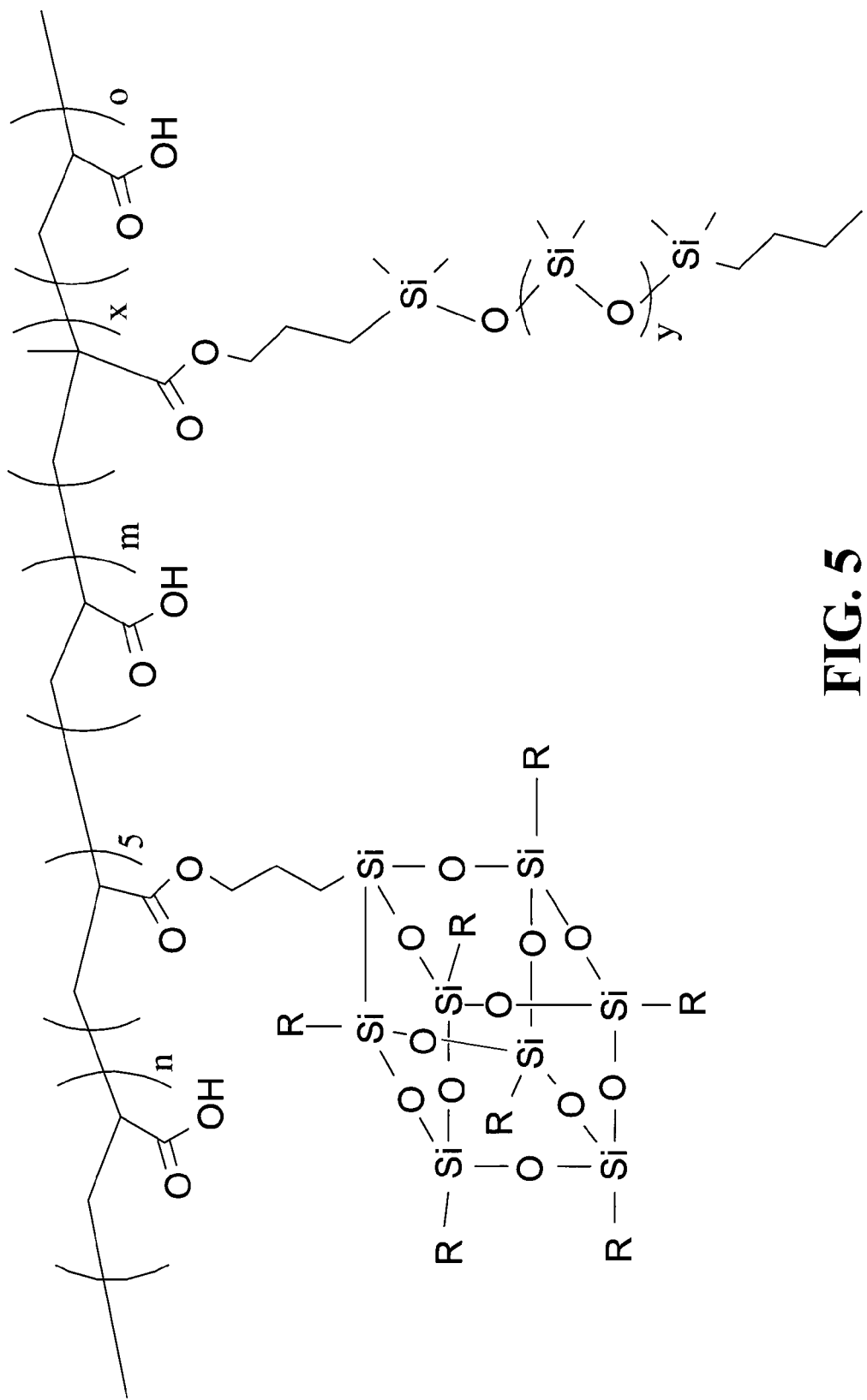
FIG. 5 is a schematic diagram showing the chemical structure of a copolymer, according to an embodiment of the present invention.

In a selected embodiment, a rheology modifying copolymer may have the chemical structure illustrated in FIG. 5, where R is i-butyl. As depicted, the number of repeating POSS monomer units is 5. In FIG. 5, m+n+o=750, which is the total number of acrylic acid monomer units. The values of m, n, and o may be random and does not need to be controlled, such that the copolymer is a random copolymer. The number averaged molecular weight (Mn) of the PDMS-MA monomers is about 4590, x is from 1 to 5, y is from 1 to 200, and the ratio of the weight of PDMS-MA to the total weight is about 7.25 to about 28.1 wt %.

In selected embodiments, a rheology modifying copolymer may be formed by polymerizing a mixture containing at least one monomer comprising a POSS compound including an ethylenically unsaturated radical; at least one ethylenically unsaturated oligo-siloxane monomer; and at least one unsaturated water-soluble monomer. In selected embodiments, the mixture to be polymerized for forming the copolymer may contain about 1 to about 30 wt % of the POSS monomer, about 1 to about 40 wt % of the oligo-siloxane monomer, and about 30 to about 98 wt % of the unsaturated water-soluble monomer, and about 0.2 to about 2 wt % of a free radical initiator, based on the total weight of the monomers.

The polymerization of the copolymer may be carried out in inert diluents such as organic fluids or mixtures of organic fluids. Suitable solvents include alcohols such as methanol, ethanol and 2-propanol; ethers such as diethyl ether, tetrahydrofuran (THF) and 1,4-dioxane; liquid hydrocarbons such as hexane and heptane; cycloalkanes such as cyclohexane; aromatics such as benzene and alkyl-substituted benzenes such as toluene and xylene; alkyl carboxylates such as ethyl acetate, isopropyl acetate, propyl acetate, methyl acetate or butyl acetate; haloalkanes such as chloro or fluoroalkanes such as methylene chloride, ethylene dichloride and chloroform, and mixtures thereof.

The copolymer may be formed in mixed solvents, e.g. THF and methanol, or dioxane and methanol, or THF and ethanol, which can be removed after the polymerization. The polymerization reactions may be initiated in the presence of a free radical initiator at a polymerization temperature of 20 to 100° C., such as 40 to 80° C.

Free radical initiators include persulfates such as sodium, potassium or ammonium persulfates, peroxygen compounds such as caprylyl peroxide, benzoyl peroxide, hydrogen peroxide, pelargonyl peroxide, cumene hydroperoxides, diisopropyl peroxydicarbonate, tertiary butyl diperphthalate, tertiary butyl perbenzoate, sodium peracetate, di-(2-ethylhexyl) peroxy dicarbonate, azo catalysts such as azobis (isobutyronitrile) and 4,4'-azobis(4-cyanovaleric acid), and the like.

As a general procedure for carrying out the polymerization reaction, a given mixture was placed in a round flask, and the flask was deoxygenated and sealed. The mixture was polymerized by heating it in a water bath at 50° C. for 1 day. The heated sample mixture was then placed into an excessive amount of diethyl ether to precipitate for purification. The precipitates were collected and dried in a vacuum oven to yield white powders.

Figure 6:
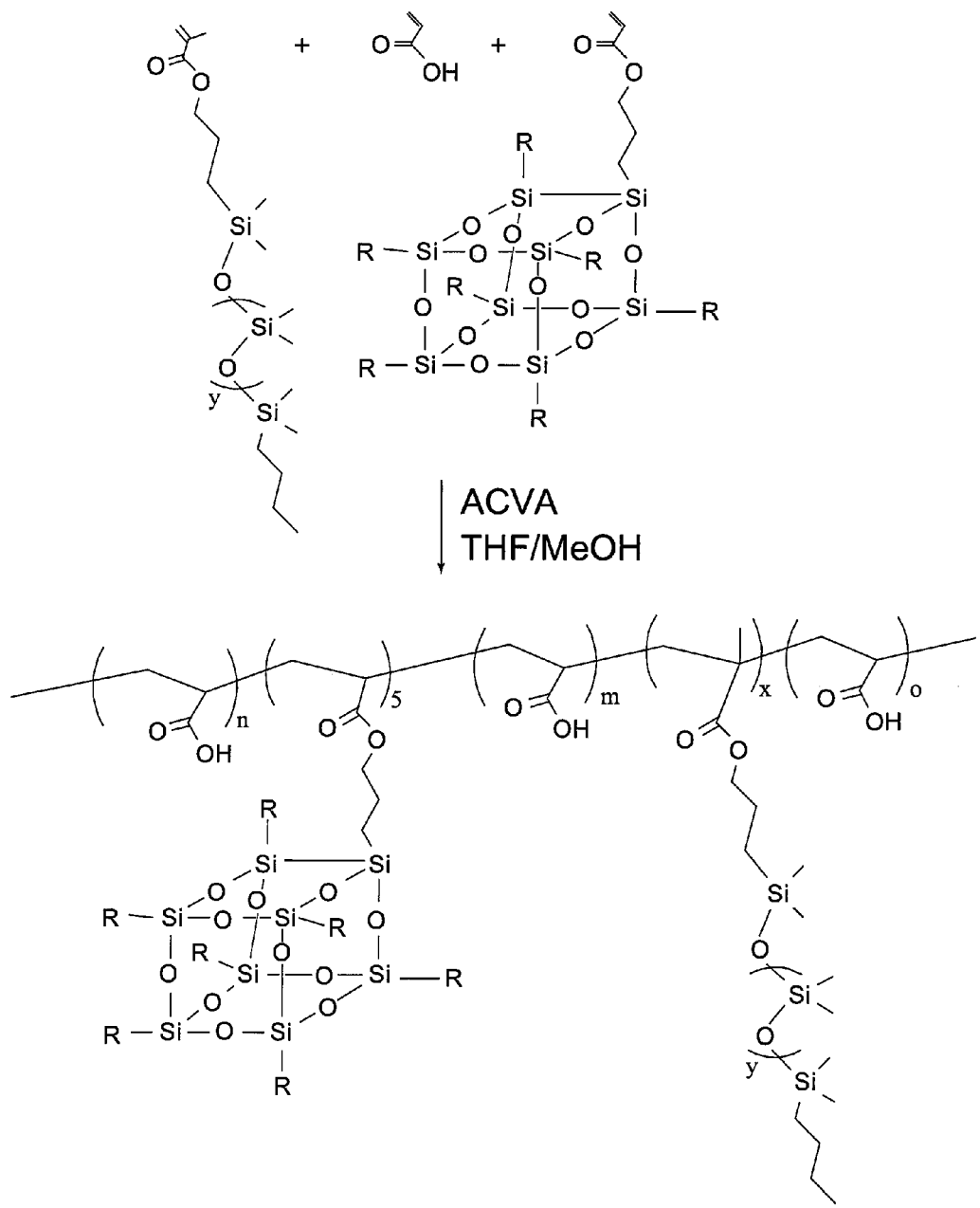
FIG. 6 is a schematic diagram illustrating a synthesis route for forming the copolymer of FIG. 5.

In a selected embodiment, a rheology modifying copolymer, such as the copolymers shown in FIG. 5, may be formed according to the synthesis route illustrated in FIG. 6. The yield of this process can be greater than 95%.

As illustrated in FIG. 6, the product of polymerization is a linear copolymer consisting essentially of acryloxy propyl isobutyl-POSS monomers, PDMS-MA monomers, and acrylic acid monomers, and may be in the form of a white powder.

In a process for forming the copolymer, a solution for polymerization may be provided, which contains about 5 to about 50 wt %, such as about 10 to about 25 wt %, of the mixture described above; about 50 to about 95 wt %, such as about 75 to 90 wt %, of a removable organic solvent; and about 0.1 to about 5 wt %, such as about 0.2 to 2 wt %, of a free radical initiator, based on total weight of the monomers.

Possible components and their respective percentages in the polymer solution are also listed in Table I. The listed concentrations are based on total weight of the monomers, except in the last row which shows the weight percentage of the solvent based on the total weight of the solvent and the monomers.

TABLE I

Contents of polymerization solution

| Components | Specific Examples | Concentration (wt %) |
|---|---|---|
| unsaturated water-soluble monomer | (meth)acrylic acid, dimethyl-aminoethyl (meth)acrylamide, dimethylaminoethyl (meth)acrylate, hydroxyethyl (meth)acrylate | 1-99, e.g. 30-98 |

TABLE I-continued

Contents of polymerization solution

| Components | Specific Examples | Concentration (wt %) |
|---|---|---|
| POSS-bearing monomer | (meth)acryloxy propyl ethyl-(isobutyl- or cyclopentyl-) POSS | 1-99, e.g. 1-30 |
| Oligo-siloxane monomer | oligo-poly(dimethyl siloxanes) (meth)acrylate | 1-99, e.g. 1-40 |
| Free radical initiator, e.g. peroxide, perester | 4,4'-Azobis(4-cyanovaleric acid), 2,2'-azobis(2-methylbutanenitrile), t-butylperoxy pivalate | 0.1-5, e.g. 0.2-2 |
| Organic solvent or mixed solvents | Methanol, ethanol, 2-propanol, THF, 1,4-dioxane, chloroform, methylene chloride | 95-50, e.g. 90-75 |

Conveniently, the copolymers described herein can be produced in a facile process that can be easily scaled-up. The components of the copolymer can provide combined effects such that the copolymer can be incorporated into a product to modify the rheology of the final product, even when the concentration of the copolymer in the final product is relatively low. In particular, the combination of POSS and PMDS-MA (unsaturated oligo-poly(dimethyl siloxane) (meth)acrylate) is shown to provide a synergistic rheology modifying effect. The inclusion of a sufficient amount of the water-soluble monomer conveniently allows the copolymer to be used in an aqueous environment or to be incorporated into a product that is to be used in an aqueous environment such as in liquids that contain water.

Possible Applications of Rheology Modifying Copolymers

Without being limited to any particular theory, it is expected that the rheology modifying effect of the copolymers may result at least in part from the mechanism discussed herein. POSS portions in the copolymer are expected to interact with hydrophobic domains of a surfactant in a solution, resulting in increased rheology. Within a limit, a higher POSS content is expected to provide a higher viscosity as more POSS portions can enter and interact with the hydrophobic domains. However, when the POSS content is higher than the limit, the copolymer molecules will tend to aggregate among themselves due to interaction between the POSS portions. As a result, less POSS portions will react with the hydrophobic domains of the surfactant, and the rheology modifying effect may be expected to decrease, instead of increase.

The copolymers described herein may have application in personal care, home care, and pharmaceutical applications. Examples of pharmaceutical applications include topical formulations in the form of creams, lotions, ointments, or gels, where the copolymers may be used as a wetting aid for the pharmaceutically active materials, or as a skin penetration enhancer, or as an emulsifier for a solvent phase having an aesthetic effect, or may be present to enhance the solubility or bioavailability of the pharmaceutically active material, or may be used as a bioadhesive agent for mucus membranes.

Embodiments of the present invention are further illustrated with the following examples, which are not intended to be limiting.

EXAMPLES

In these examples, various sample copolymers were polymerized from different monomeric mixtures whose contents are listed in Table II. The values given are the weight percentages of the respective components based on the total weight of the mixture except the solvent.

TABLE II

| Sample | AA | POSS-A | PDMS-MA | ACVA | Solvent (1/1) | T (° C.) | Time (day) | Viscosity (1% sample in 12% SDS) (cps) |
|---|---|---|---|---|---|---|---|---|
| 1 | 88.4 | 7.6 | 3.8 | 0.2 | THF/MeOH | 50 | 1 | 14.1 |
| 2 | 76.9 | 6.6 | 16.3 | 0.2 | THF/MeOH | 50 | 1 | 15.0 |
| 3 | 59.4 | 5.1 | 35.3 | 0.2 | THF/MeOH | 50 | 1 | 15.3 |
| 4 | — | — | — | — | — | — | — | 1.45 |

In Table II and the description below, AA=acrylic acid; POSS-A=acryloxy propyl isobutyl-POSS; PDMS-MA=oligo-poly(dimethyl siloxanes)methacrylate ($M_n$=4587); ACVA=4,4'-azobis(4-cyanovaleric acid); and SDS=sodium n-dodecyl sulfate. Sample 4 was a control sample used for viscosity testing at 12% SDS solution.

Example 1

2 g of AA, 172 mg of POSS-A, 85 mg of PDMS-MA and 5.2 mg of ACVA were dissolved by 5 mL of THF and 5 mL MeOH mixed solvent in a 50 mL round flask. The contents in the flask were deoxygenated by argon bubbling for half an hour and sealed. The mixture in the flask was stirred at 50° C. for one day, and the heated mixture was precipitated into 300 mL of ether. The white powder (Sample 1) was collected by ultrafiltration and dried at 50° C. under vacuum for two days.

Example 2

2 g of AA, 172 mg of POSS-A, 424 mg of PDMS-MA and 5.2 mg of ACVA were dissolved by 5 mL THF and 5 mL MeOH mixed solvent in a 50 mL round flask. The contents in the flask were deoxygenated by argon bubbling for half an hour and sealed. The mixture in the flask was stirred at 50° C. for one day, and the heated mixture was precipitated into 300 mL of ether. The white powder (Sample 2) was collected by ultrafiltration and dried at 50° C. under vacuum for two days.

Figure 7:
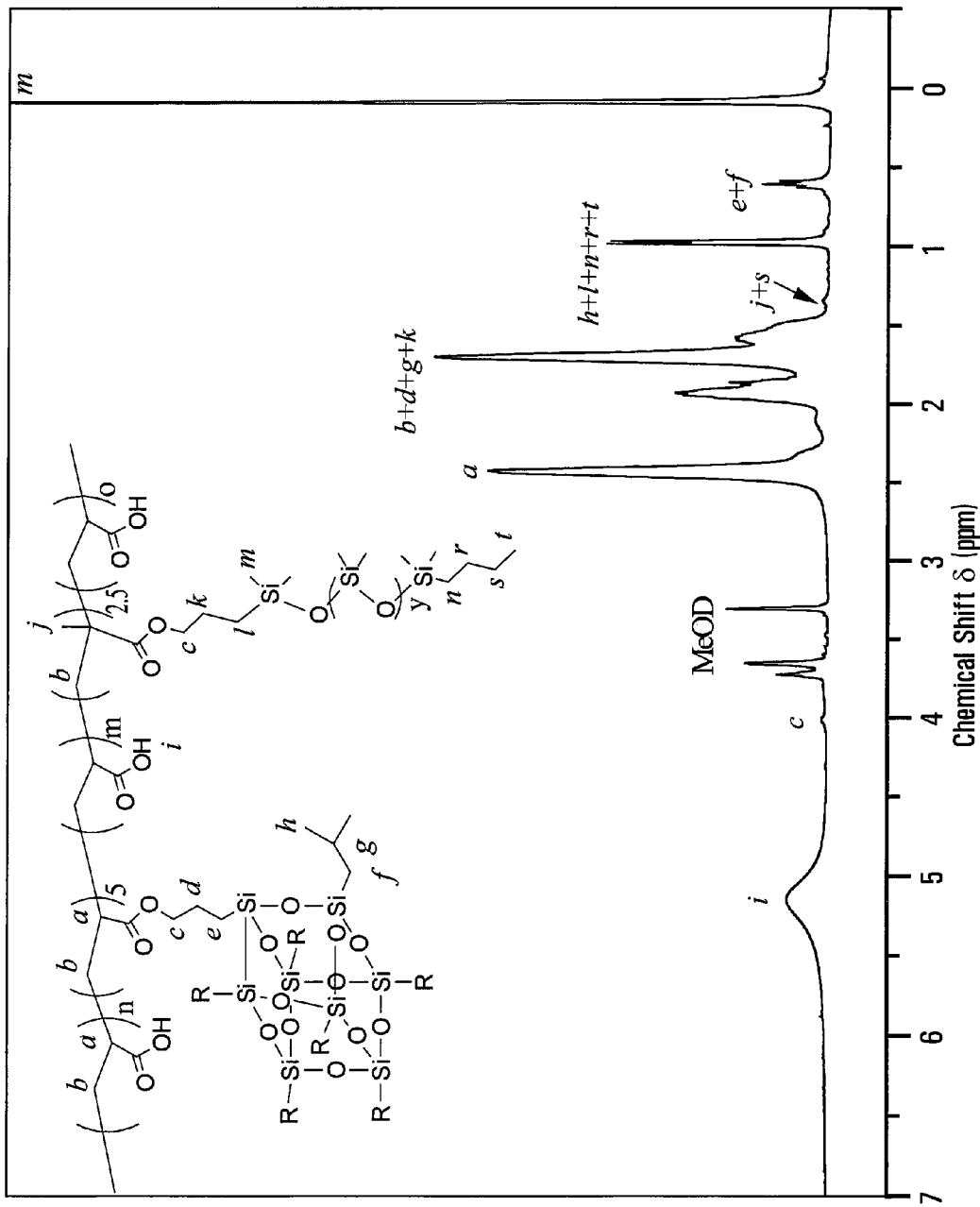
FIG. 7 is a $^1$H-NMR spectrum of a sample copolymer.

A measured $^1$H-NMR spectrum of Sample 2 and the chemical structure of copolymer in Sample 2 are shown in FIG. 7.

Figure 8:
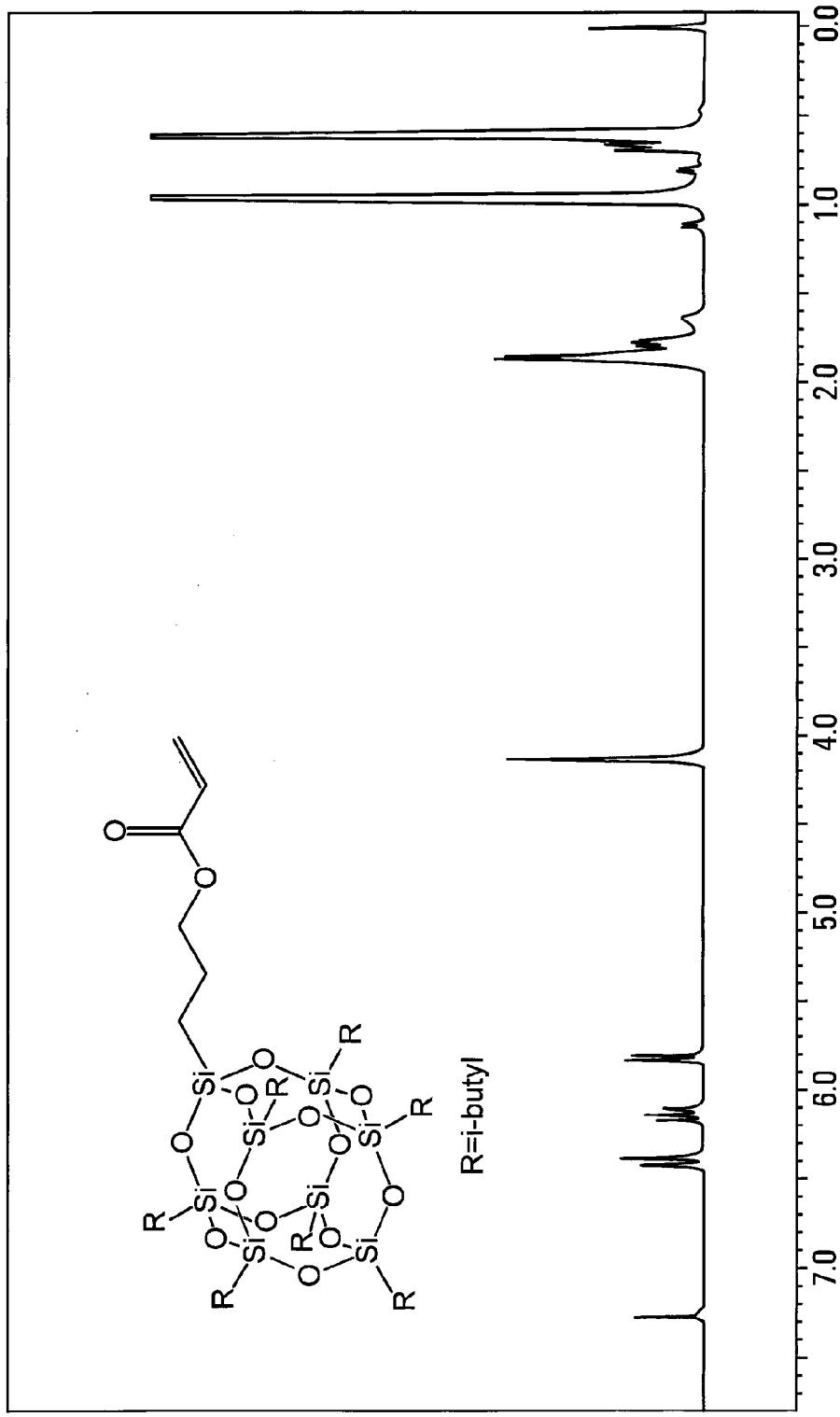
FIG. 8 is a $^1$H-NMR spectrum of a sample POSS monomer.

In comparison, the $^1$H-NMR spectrum of a POSS-A monomer is shown in FIG. 8.

Example 3

2 g of AA, 172 mg of POSS-A, 1.188g of PDMS-MA and 5.2 mg of ACVA were dissolved by 5 mL THF and 5 mL MeOH mixed solvent in a 50 mL round flask. The contents in the flask were deoxygenated by argon bubbling for half an hour and sealed. The mixture in the flask was stirred at 50° C. for one day, and the heated mixture was precipitated into 300 mL of ether. The white powder (Sample 3) was collected by ultrafiltration and dried at 50° C. under vacuum for two days.

Example 4

A 1% stock dispersion of Sample 1, 2 or 3 (1 g) was prepared in 12% sodium n-dodecyl sulfate (SDS) solution (99 g). In each case, the mixture was stirred at room temperature for over 3 days to form a homogeneous solution.

The viscosity of the dispersion was then measured using a Rheometer Rheostress 600 (THERMO HAAKE™) at 20 rpm. The measured results are summarized in Table II and the viscosity values were determined to be around 15 cps for all three Samples 1, 2, and 3. In comparison, the viscosity of 12% SDS solution without adding the copolymer (Sample 4) was found to be about 1.45 cps. With adding 1 wt % of the sample copolymer, the viscosity of the final solution was enhanced to be about ten times higher than the original surfactant solution.

It will be understood that any singular form is intended to include plurals herein. For example, the word "a", "an" or "the" is intended to mean "one or more" or "at least one." Plural forms may also include a singular form unless the context clearly indicates otherwise.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used. For any list of possible elements or features provided in this specification, any sub-list falling within the given list is also intended.

Similarly, any range of values given herein is intended to specifically include any intermediate value or sub-range within the given range, and all such intermediate values and sub-ranges are individually and specifically disclosed.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A copolymer for modifying rheology, formed of monomer units consisting essentially of:
   at least one first monomer unit comprising a polyhedral oligomeric silsesquioxane having an ethylenically unsaturated radical;
   at least one second monomer unit comprising an unsaturated oligo-poly(dimethyl siloxane)(meth)acrylate; and
   a sufficient amount of at least one unsaturated water-soluble monomer, such that said copolymer is soluble in water.

2. The copolymer of claim 1, comprising:
   about 1 to about 30 wt % of said at least one first monomer unit;
   about 1 to about 40 wt % of said at least one second monomer unit; and
   about 30 to about 98 wt % of said at least one unsaturated water-soluble monomer,
   based on the total weight of said monomer units and said at least one unsaturated water-soluble monomer.

3. The copolymer of claim 1, comprising:
   about 5 to about 8 wt % of said at least one first monomer unit;
   about 4 to about 35 wt % of said at least one second monomer unit; and
   about 60 to about 90 wt % of said at least one unsaturated water-soluble monomer,
   based on the total weight of said monomer units and said at least one unsaturated water-soluble monomer.

4. The copolymer of claim 1, wherein said at least one first monomer unit comprises a monomer unit of formula (I):

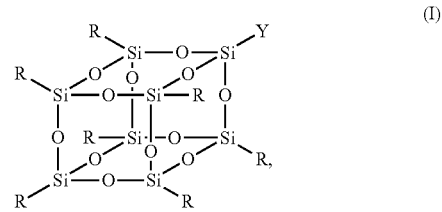

wherein
   Y is independently an ethylenically unsaturated radical; and
   each R is independently a $C_1$-$C_{12}$ monovalent hydrocarbon radical, a $C_1$-$C_{12}$ monovalent hydrocarbon radical comprising an ether linkage, a halogen-substituted $C_1$-$C_{12}$ monovalent hydrocarbon radical, or a halogen-substituted $C_1$-$C_{12}$ monovalent hydrocarbon radical comprising an ether linkage.

5. The copolymer of claim 4, wherein Y is acryloxypropyl, and each R is i-butyl.

6. The copolymer of claim 1, wherein said at least one first monomer unit comprises a monomer unit of formula (II), (III), or (IV):

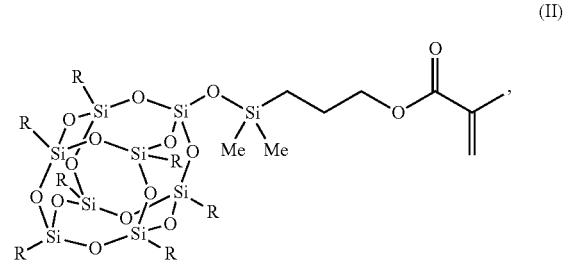

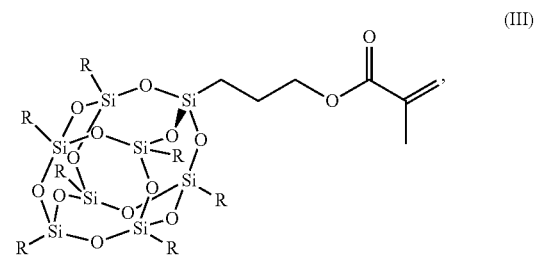

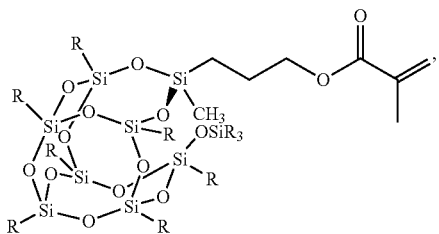

(IV)

wherein each R is independently a $C_1$-$C_{12}$ monovalent hydrocarbon radical, a $C_1$-$C_{12}$ monovalent hydrocarbon radical comprising an ether linkage, a halogen-substituted $C_1$-$C_{12}$ monovalent hydrocarbon radical, or a halogen-substituted $C_1$-$C_{12}$ monovalent hydrocarbon radical comprising an ether linkage.

7. The copolymer of claim 6, wherein each R is i-butyl.

8. The copolymer of claim 1, comprising 5 repeating units of said at least one first monomer unit.

9. The copolymer of claim 1, wherein said at least one second monomer unit comprises a monomer unit of formula (V):

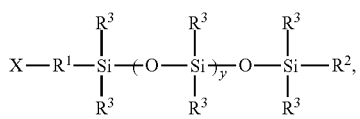

(V)

wherein
X is an activated unsaturated radical;
$R^1$ is a $C_1$-$C_{22}$ divalent hydrocarbon radical;
$R^2$ is a $C_1$-$C_{22}$ monovalent hydrocarbon radical;
each $R^3$ is methyl; and
y is from 1 to 200.

10. The copolymer of claim 9, wherein X is (meth)acryloxy, $R^1$ is propylene, and $R^2$ is n-butyl.

11. The copolymer of claim 1, comprising 1 to 5 repeating units of said at least one second monomer unit.

12. The copolymer of claim 1, wherein said at least one unsaturated water-soluble monomer comprises a monomer having the formula (VI):

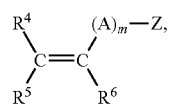

(VI)

wherein
m is an integer from 0 to 10;
A is a methylene group;
$R^4$ is a hydrogen atom, a phenyl group, or a benzyl group;
$R^5$ is a hydrogen atom, or a lower alkyl or carboxyl group;
$R^6$ is a hydrogen atom, a lower alkyl group, —$CH_2COOH$, a phenyl group, a benzyl group, or a polymeric group comprising a unit derived from a sulfonic acid; and
Z is COOH, COO(B)$_n$Y$^1$, or CON($R^7$)$R^8$, wherein
$R^7$ and $R^8$ is each independently hydrogen or (B)$_n$Y$^1$;
B is a methylene group;
n is an integer from 1 to 10; and
$Y^1$ is a hydroxyl group, primary amine, secondary amine, tertiary amine, or quaternary ammonium salt.

13. The copolymer of claim 1, wherein said at least one unsaturated water-soluble monomer comprises a carboxylic acid.

14. The copolymer of claim 1, wherein said at least one unsaturated water-soluble monomer is an acrylic acid.

15. The copolymer of claim 1, wherein said copolymer is a random copolymer, a block copolymer, or a graft copolymer.

16. A composition comprising an electrolyte and a copolymer for modifying rheology, formed of monomer units consisting essentially of:
at least one first monomer unit comprising a polyhedral oligomeric silsesquioxane having an ethylenically unsaturated radical;
at least one second monomer unit comprising an unsaturated oligo-poly(dimethyl siloxane)(meth)acrylate; and
a sufficient amount of at least one unsaturated water-soluble monomer, such that said copolymer is soluble in water.

17. A method of modifying the rheology of an environment comprising an electrolyte, the method comprising adding a copolymer for modifying rheology, formed of monomer units consisting essentially of:
at least one first monomer unit comprising a polyhedral oligomeric silsesquioxane having an ethylenically unsaturated radical;
at least one second monomer unit comprising an unsaturated oligo-poly(dimethyl siloxane)(meth)acrylate; and
a sufficient amount of at least one unsaturated water-soluble monomer, such that said copolymer is soluble in water, to the environment.

18. The method of claim 17, wherein the environment comprises a solution and the copolymer is added to the solution.

* * * * *